US00PP15111P2

(12) United States Plant Patent
Olesen et al.

(10) Patent No.: US PP15,111 P2
(45) Date of Patent: Aug. 24, 2004

(54) GROUND COVER ROSE PLANT 'POULTW001'

(50) Latin Name: *Rosa hybrida*
Varietal Denomination: POULtw001

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 10/341,894

(22) Filed: Jan. 13, 2003

(51) Int. Cl.[7] ..... A01H 5/00
(52) U.S. Cl. ..... Plt./108
(58) Field of Search ..... Plt./108

(56) References Cited

U.S. PATENT DOCUMENTS

PP13,270 P2 * 11/2002 Olesen et al. ..... Plt./108

OTHER PUBLICATIONS

UPOV ROM GTITM Computer Database, GTI JOUVE Retrieval Software 2003/03 Citation for 'POULtw001'.*

* cited by examiner

*Primary Examiner*—Bruce R. Campell
*Assistant Examiner*—W C Haas

(57) ABSTRACT

A new ground cover garden rose plant which has abundant, red flowers and attractive foliage. This new and distinct variety has shown to be uniform and stable in the resulting generations from asexual propagation.

1 Drawing Sheet

Classification: Botanical: *Rosa hybrida* 'POULtw001'. Commercial: Ground cover rose.

SUMMARY OF THE INVENTION

The present invention constitutes a new and distinct variety of garden rose plant which originated from a controlled crossing between a non-patented variety 'POULsint' and 'Kormixal Suffolk', a non-patented variety which is not the subject of a US Patent application that we are aware of. The two parents were crossed during the summer of 1993 and the resulting seeds were planted in a controlled environment in Fredensborg, Denmark. The new variety is named 'POULtw001'.

The new variety may be distinguished from its pollen parent, 'Kormixal Suffolk' by the following combination of characteristics:

1. 'POULtw001' exhibits dark red blooms while 'Kormixal Suffolk' exhibits lighter red blooms with a yellow center.

The new variety may be distinguished from its seed parent, 'POULsint' by the following combination of characteristics:

1. 'POULtw001' exhibits dark red blooms while 'POULsint' exhibits medium red flowers.
2. 'POULtw001' has under 15 petals while 'POULsint' has 15 to 25 petals.

The objective of the hybridization of this rose variety was to create a new and distinct variety for garden use with unique qualities, such as:

1. Uniform and abundant flowers;
2. Vigorous, but compact growth when propagated both as a budded rose and on its own roots;
3. Disease resistance.

This combination of qualities is not present in previously available commercial cultivars of this type, known to the inventors, and distinguish 'POULtw001' from all other varieties of which we are aware.

As part of their rose development program, L. Pernille Olesen and Mogens N. Olesen germinated the seeds from the aforementioned hybridization during winter 1994 and conducted evaluations on the resulting seedlings in a controlled environment in Fredensborg, Denmark.

'POULtw001' was selected in the spring 1994 by the inventors as a single plant from the progeny of the aforementioned hybridization.

Asexual reproduction of 'POULtw001' by traditional budding and rooted cuttings was first done by L. Pernille and Mogens N. Olesen in their nursery in Fredensborg, Denmark in August, 1994. This initial and other subsequent asexual propagations conducted in controlled environments have demonstrated that the characteristics of 'POULtw001' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'POULtw001'. Specifically illustrated in the drawing:

1. Stem showing branching and the attachment of leaves, buds, and peduncles;
2. Flower bud, partially opened bud, and open bloom;
3. Flower petals, detached;
4. Sepals, receptacle, and pedicel;
5. Stem as well as a bare stem exhibiting thorns;
6. Leaves.

DETAILED DESCRIPTION OF THE VARIETY

The following is a description of 'POULtw001', as observed in its growth in a field nursery in Jackson County, Oreg. Observed plants are 3 years of age. Color references are made using The Royal Horticultural Society (London, England) Colour Chart, 1995, except where common terms of color are used.

For a comparison, several physical characteristics of the rose variety 'POULattra', a rose variety from the same inventors described and illustrated in U.S. Plant Pat. No. 13,270 and issued on November 26, are compared to 'POULtw001' in Chart 1.

CHART 1

| | 'POULtw001' | 'POULattra' |
|---|---|---|
| Average range of petalage | 13 to 15 petals | 20 to 25 petals |
| Color of open blooms | Red Group 45B | Red Group 53A |
| Color of petal spots | White Group 155D | Yellow Group 4D |

Parents:

*Seed parent.*—'POULsint'.

*Pollen parent.*—'Kormixal Suffolk'.

FLOWER AND FLOWER BUD

Blooming habit:Continuous.

Flower bud:

*Size.*—Upon opening, 20 mm in length from base of receptacle to end of bud. Bud diameter is 8 mm.

*Bud form.*—Pointed ovoid.

*Bud color.*—As sepals unfold, petals are Red Group 45B. At ¼ opening, petals are Red Group 45B.

*Sepals.*—Green Group 143B. Weak foliaceous appendages on three of the five sepals. Surfaces of sepals moderately pubescent. Stipitate glands are present along the receptacle and margins of the sepals and stipules. Shape: Sepal apex is cirrhose. Base is flat at union with peduncle. General sepal shape is subulate with an extended apex. Margins: Foliaceous appendages up to 4 mm in length extend from the margins of the sepals. Size: 15 mm long×5 mm wide.

*Receptacle.*—Surface: Smooth with light pubescence. Shape: Urn-shaped. Size: Small. 5 mm (h)×5 mm (w). Color: Yellow-Green Group 144B with intonations of Greyed-Red Group 181B.

*Peduncle.*—Surface: Smooth with sparse pubescence. Stipitate glands are mildly fragrant. Length: 28 mm average length. Diameter: 2 mm. Color: Yellow-Green Group 144B with light intonations of Greyed-Red Group 181B. Strength: Weak.

*Borne.*—Multiples of 3 to 4 buds per stem.

*Anthocyanin.*—Color: Greyed-Red Group 181B.

Flower bloom:

*Fragrance.*—Light wild rose scent.

*Duration.*—The blooms have a duration on the plant of approximately 7 to 10 days. Petals fall cleanly away from plant.

*Size.*—Average flower diameter is 40 mm when open. Flowers are 18 mm in depth.

Form:

*Shape of flower when viewed from the side.*—Upon opening, upper part: Flattened convex. Upon opening, lower part: Convex. Open flower, upper part: Flattened convex. Open flower, lower part: Convex.

*Petalage.*—Semi-double. Average range: 13 to 15 petals under normal conditions with 6 petaloids.

Color:

*Upon opening, petals.*—Outermost petals: Outer side: Red Group 45B. Inner Side: Red Group 45B. Innermost petals: Outer side: Red Group 45B. Inner Side: Red Group 45B.

*Upon opening, basal petal spots.*—Outermost petals: Outer side: White Group 155D. Inner Side: White Group 155D. Innermost petals: Outer side: White Group 155D. Inner Side: White Group 155D.

*After opening, petals.*—Outermost petals: Outer side: Red Group 45B. Inner Side: Red Group 45B. Innermost petals: Outer side: Red Group 45B. Inner Side: Red Group 45B.

*After opening, basal petal spots.*—Outermost petals: Outer Side: White Group 155D. Inner Side: White Group 155D. Innermost petals: Outer Side: White Group 155D. Inner Side: White Group 155D.

General tonality: On open flower Red Group 45B. No change in the general tonality at the end of the 10th day. Afterwards, general tonality is Red Group 45B.

Petals:

*Petal reflex.*—Reflexed slightly.

*Petal edge.*—Uniform and typically ruffled slightly along margin.

*Shape.*—General shape is deltoid. Petal apex is rounded. The petal base shape is acute, to somewhat rounded.

*Texture.*—Smooth.

*Size.*—17 mm length×15 mm wide.

*Thickness.*—Thin.

*Petaloids.*—Quantity: 6 to 10. Shape: Elliptical with asymmetrical irregularities. Size: 9 mm in length by 5 mm wide.

*Arrangement.*—Not Formal.

Reproductive organs:

*Pistils.*—Length: 4 mm long. Quantity: Range is 25 to 30. Color: Yellow-Green Group 145B at the base. Greyed-Purple 186B observed at the upper portion of the pistil.

*Pollen.*—Quantity: None observed.

*Anthers.*—Size: 2 mm long. Color: Red Group 46A with intonations of Yellow-Orange Group 17A at margins. Quantity: 84.

*Filaments.*—Color: Yellow-Green Group 144D. Length: 6 mm.

*Stigmas.*—The height of the stigmas is equal to and, occasionally, superior to the height of the anthers. Color: Greyed-Yellow Group 161C.

*Styles.*—Color: Yellow-Green Group 144D. Other intonations: At top of styles and extending into the anthers Red Group 48A. Quantity: Range is 25 to 30.

*Hips.*—None observed.

PLANT

Plant growth: Compact to bushy. When grown as a nursery plant on its own roots the average plant height is 70 to 100 cm and the average plant width is 70 cm.

Stems:

*Color.*—Young wood: Yellow-Green Group 144B. Older wood: Yellow-Green Group 144B.

*Length.*—60 cm. Diameter: 10 mm. Internodes: 45 to 50 mm.

*Thorns.*—Incidence: 38 thorns per 10 cm of stem. Size: Average length: 8 mm. Color: Red Group 46A. Shape: Concave.

*Surface.*—Young wood: Smooth. Older wood: Smooth.

Plant foliage: Normal number of leaflets on normal leaves in middle of the stem: 7 leaflets.

*Leaf size.*—22 mm (l)×14 mm (w).

*Quantity.*—Average. 2 leaves per 10 cm of stem observed.

*Color.*—Mature Foliage: Upper Leaf Surface: Green Group 143A. Lower Leaf Surface: Yellow-Green Group 145A. Juvenile foliage: Upper Leaf Surface: Green Group 143A. Lower Leaf Surface: Yellow-Green Group 145A. Anthocyanin intonation: Location: Limited to peduncles. Color: Greyed-Red Group 181B.

Plant leaves and leaflets:

*Stipules.*—Size: 15 mm in length. Color: Yellow-Green Group 144A. Quantity: 2 per compound leaf. Shape: Stipules are linear, with outward and upward extending apecies. Margins: Deeply serrated with stipitate glands. Anthocyanin: Not observed.

*Petiole.*—Length: 15 mm. Diameter: 1.5 mm. Color: Yellow-Green Group 144B. Margins: Stipitate glands present. Anthocyanin: Greyed-Red 181A.

*Rachis.*—Color: Yellow-Green Group 144B. Length: 50 mm. Margins: Stipitate glands in small quantity. Anthocyanin: Light intonations of Greyed-Red Group 181A.

*Leaflet.*—Size: Terminal leaflets are 32 mm in length and 22 mm wide. Edge: Serrated. Shape: Ovate. The leaflet apex is acute to somewhat cuspidate. The leaflet base shape is rounded. Texture: Moderately glossy with medium thickness. Arrangement: Odd pinnate. Venation: Reticulate. Leaf veins are Yellow-Green Group 144C in color with anthocyanic intonations of Greyed-Purple 183C.

Disease resistance: Above average resistance to mildew, rust, black spot, and Botrytis under normal growing conditions in Jackson County, Oreg.

Cold hardiness: The variety 'POULtw001' has been found to be cold tolerant to USDA cold hardiness zone 7 in Jackson County, Oreg.

We claim:

1. A new and distinct variety of rose plant of the ground cover rose class, substantially as herein illustrated and described as a distinct and novel rose variety due to its abundant red flowers, disease resistance, and extended period of bloom.

* * * * *

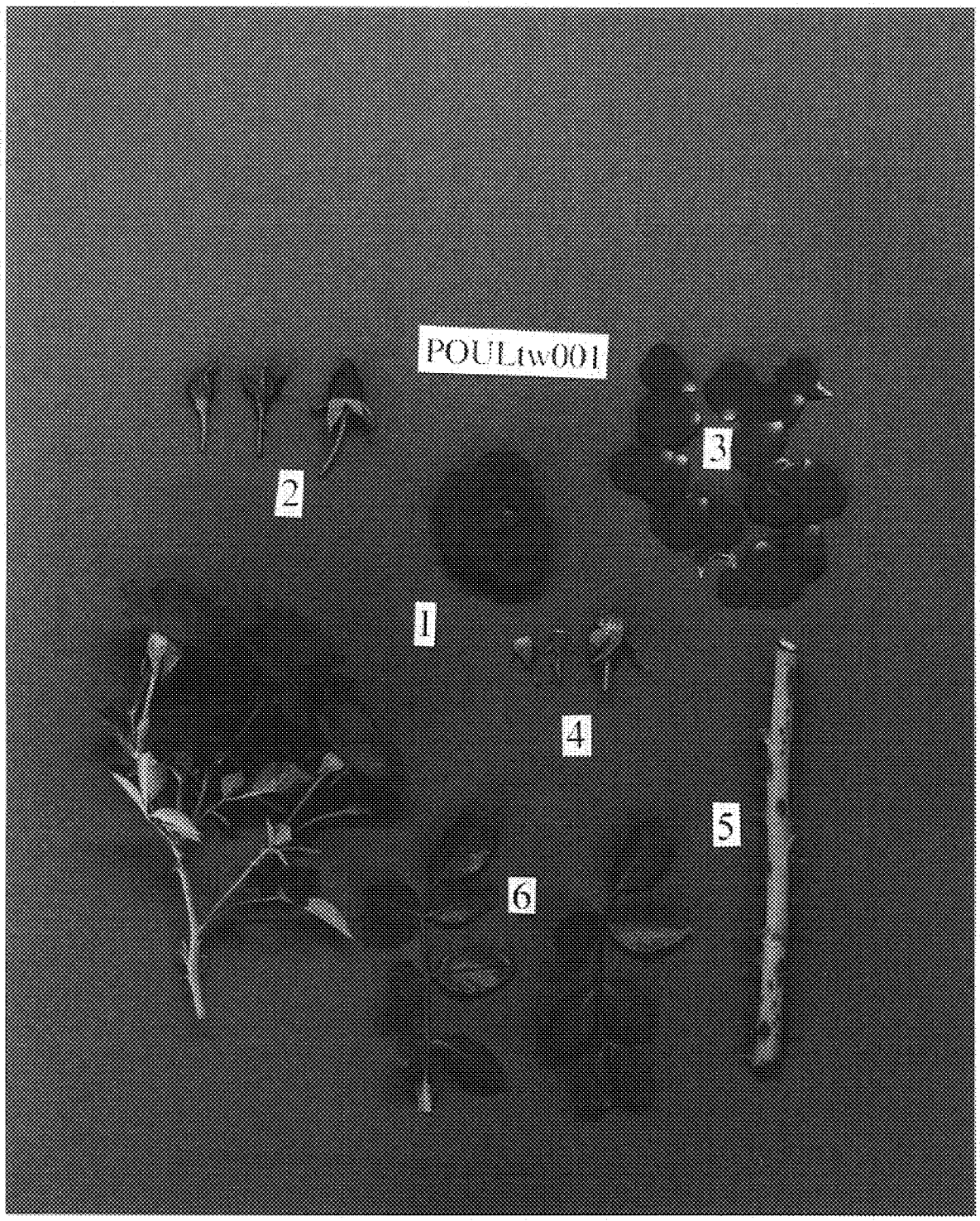
POULtw001
1
2
3
4
5
6